(12) United States Patent
Perlman

(10) Patent No.: US 11,788,045 B2
(45) Date of Patent: *Oct. 17, 2023

(54) POLYLACTIDE CELL CULTURE CONTAINERS AND USE IN CELL CULTURE

(71) Applicant: Diversified Biotech, Inc., Dedham, MA (US)

(72) Inventor: Daniel Perlman, Arlington, MA (US)

(73) Assignee: Diversified Biotech, Inc., Dedham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/701,045

(22) Filed: Mar. 22, 2022

(65) Prior Publication Data

US 2022/0213423 A1 Jul. 7, 2022

Related U.S. Application Data

(63) Continuation-in-part of application No. 16/705,920, filed on Dec. 6, 2019, now Pat. No. 11,279,909.

(51) Int. Cl.
*C12M 1/00* (2006.01)
*C12M 1/12* (2006.01)
*C08L 67/04* (2006.01)

(52) U.S. Cl.
CPC .............. *C12M 23/30* (2013.01); *C08L 67/04* (2013.01); *C12M 23/22* (2013.01); *C12M 23/28* (2013.01); *C12M 25/14* (2013.01)

(58) Field of Classification Search
None
See application file for complete search history.

(56) References Cited

U.S. PATENT DOCUMENTS

| 11,279,909 B2 * | 3/2022 | Perlman | C12M 23/08 |
| 2003/0069629 A1 * | 4/2003 | Jadhav | A61F 2/90 |
| | | | 623/1.15 |
| 2007/0187876 A1 * | 8/2007 | Cink | B29C 49/0005 |
| | | | 264/510 |
| 2007/0249044 A1 | 10/2007 | Desai et al. | |
| 2008/0140094 A1 | 6/2008 | Schwartz et al. | |
| 2008/2093135 | 11/2008 | Orr et al. | |

(Continued)

FOREIGN PATENT DOCUMENTS

EP 2746318 A1 6/2014
JP 2004204195 A * 7/2004

(Continued)

OTHER PUBLICATIONS

Srithep et al. "Effects of Annealing Time and Temperature on the Crystallinity and Heat Resistance Behavior of Injection-Molded Poly(lactic acid)." Polymer Engineering and Science—2013, pp. 580-588. (Year: 2013).*

(Continued)

*Primary Examiner* — William H. Beisner
(74) *Attorney, Agent, or Firm* — Verrill Dana, LLP

(57) ABSTRACT

2D and 3D cell culture containers formed from blends of poly-L-lactide and poly-D-lactide provide growth surfaces for adherent cells and do not require surface treatment or coating to support mammalian cell growth. The cell culture (Continued)

containers are transparent, heat tolerant, and are environmentally degradable and suitable for composting in landfills.

20 Claims, 1 Drawing Sheet

(56) References Cited

U.S. PATENT DOCUMENTS

| | | |
|---|---|---|
| 2009/0123434 A1 | 5/2009 | Ross |
| 2009/0233356 A1 | 9/2009 | Mcallister et al. |
| 2010/0028992 A1 | 2/2010 | Wang et al. |
| 2010/0120145 A1 | 5/2010 | Brunner et al. |
| 2010/0136685 A1 | 6/2010 | Hsieh et al. |
| 2010/0331216 A1 | 12/2010 | Sokabe et al. |
| 2011/0045500 A1 | 2/2011 | Taniguchi et al. |
| 2011/0160869 A1 | 6/2011 | Duch et al. |
| 2011/0318829 A1 | 12/2011 | Tazaki et al. |
| 2012/0009103 A1* | 1/2012 | Liu .................. B01L 3/00 264/537 |
| 2013/0096491 A1 | 4/2013 | Suzuki |
| 2013/0115691 A1 | 5/2013 | Schryver |

FOREIGN PATENT DOCUMENTS

| | | |
|---|---|---|
| JP | 2009000012 A | 1/2009 |
| WO | 2013117626 A1 | 8/2013 |

OTHER PUBLICATIONS

Pardo, Amp. et al. "Corning CellBIND Surface: an Improved Surface for Enhanced Cell Attachment", Corning Technical Report, 2005, 8 page report.

Koo, GH et al. "Surface modification of poly(lactic acid) by UV/Ozone irradiation", Fibers and Polymers, 9, 674-678 (2008) *Abstract Only*.

Milicevic, D. et al., "The resistance of poly-(l-lactide) to gamma radiation: effect of initial preparation and crystallinity", Polymer Bulletin (2020), 77:2659-2677 doi.org/10.1007/s00289-019-02880-2.

Milicevic, D. et al., "Thermal and crystallization behaviour of gamma irradiated PLLA", Radiation Physics and Chemistry 76 (2007) 1376-1380 DOI:10.1016/j.radphyschem.2007.02.035.

Zaidi, L. et al., "The effects of gamma irradiation on the morphology and properties of polylactide/Cloisite 30B nanocomposites", Polymer Degradation and Stability 98 (2013) 348-355.

Costa et al., "Maintenance of chondrocyte phenotype during expansion on PLLA microtopographies" Journal of Tissue Engineering, vol. 9 (Aug. 6, 2018): pp. 1-10 (Year 2018).

M. Savaris et al., "Influence of different sterilization processes on the ofcommercial poly(lactic acid)", Materials Science and Engineering, C60 (2016), pp. 661-667. (Year 2016).

* cited by examiner

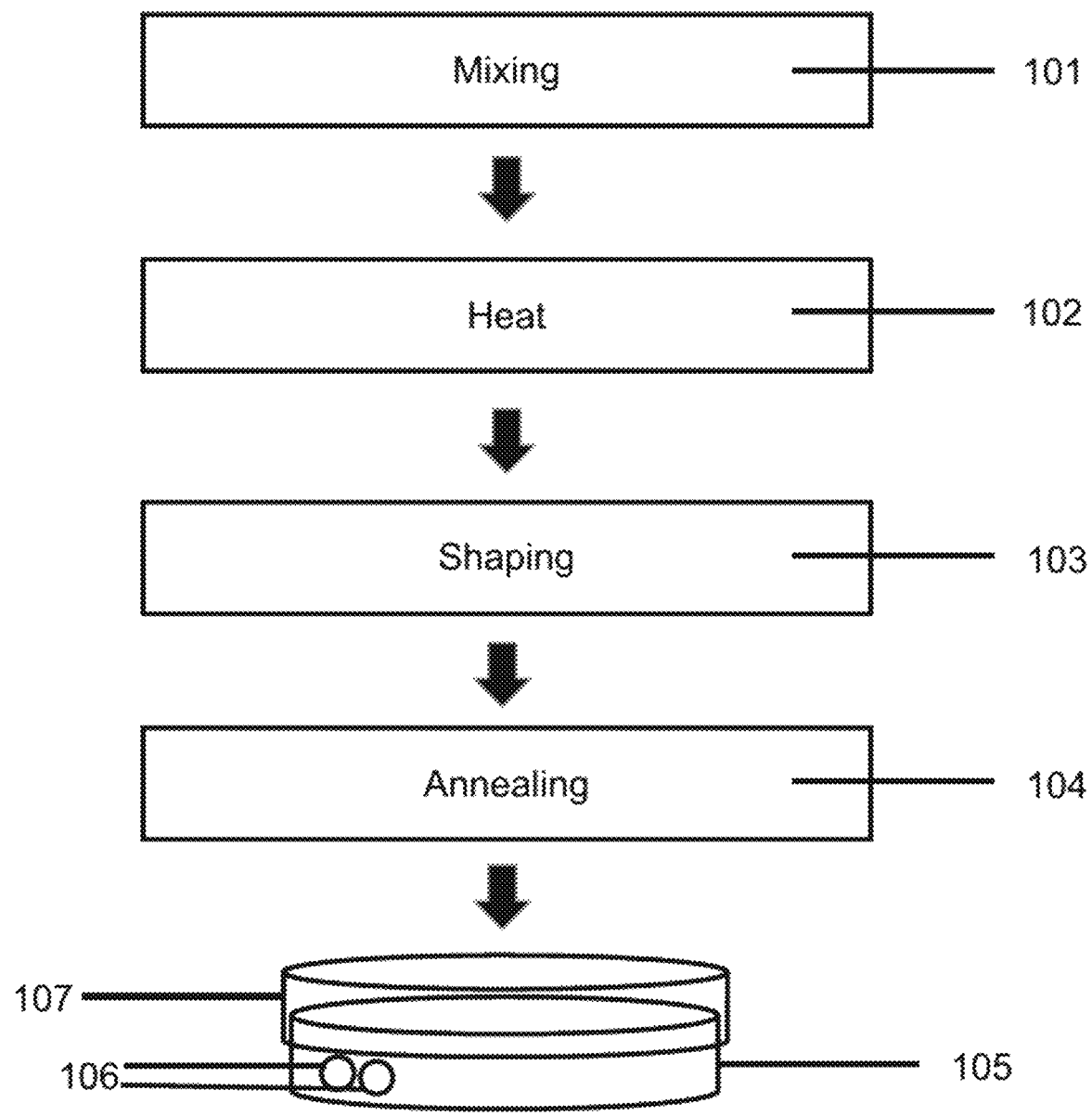

POLYLACTIDE CELL CULTURE CONTAINERS AND USE IN CELL CULTURE

CROSS-REFERENCE TO RELATED APPLICATION

This application is a continuation in part of U.S. Pat. No. 11,279,909, which was filed on 6 Dec. 2019 and issued on 22 Mar. 2022, which is hereby incorporated by reference in its entirety.

BACKGROUND

Pre-sterilized disposable plastic cell culture containers have become ubiquitous for culturing of eukaryotic and prokaryotic cells. These plastic cell culture containers are usually fabricated from synthetic polymer resins including polystyrene, polyvinyl, polycarbonate, and polyolefin-type (polyethylene and polypropylene) thermoplastics. One major problem arising from the ubiquitous and large-scale use of plastic cell culture containers is that of environmental sustainability. Commercial sterilization of such thermoplastic products is routinely accomplished using either gamma irradiation, electron-beam irradiation, or ethylene oxide treatment. With few exceptions, plastic cell culture containers are difficult or impossible to reuse because they would require washing and re-sterilization, in which generally available laboratory sterilization equipment (e.g., steam autoclaves) would melt or severely distort most of the conventionally used plastics described above that have relatively low softening and melting temperatures. Consequently, these plastic cell culture containers are usually discarded in landfills or destroyed by incineration after use. Landfill disposal is undesirable because petroleum-derived synthetic plastics do not readily decompose or compost, and incineration can produce toxic gases. Thus, there is an urgent need for cell culture containers that are environmentally degradable and suitable for landfill compost or disposal.

When most types of conventional cell culture vessels are used to grow anchorage-dependent animal or plant cells (also referred to as attachment-dependent or adherent cells), an interior surface of the culture vessel has to be pre-treated, modified, or coated to promote cellular attachment, without which many cell types will not grow. While an untreated polystyrene Petri dish may be useful for culturing bacteria and yeast cells on a solid nutrient agar, for example, the untreated polystyrene dish is not a useful or functional container for growing anchorage-dependent mammalian cells. Various surface treatments and coatings for promoting cellular attachment to polystyrene cell culture containers are known. Such treatments, coatings, or modifications can significantly add to the cost and complexity of producing a cell culture container. The cost can rapidly increase for large 2D growth surfaces or for complex 3D growth surfaces. Thus, there is a need for cell culture containers that do not require surface treatments, coatings, or modifications for successful cultivation of anchorage-dependent animal or plant cells, while still providing cellular attachment and robust cell anchorage.

SUMMARY

The present technology provides cell culture containers that can be utilized for cultivating prokaryotic or eukaryotic cells, including adherent cells, such as adherent mammalian cells, without requiring surface treatment of the containers after they have been molded from thermoplastic resin. Growth surfaces of the cell culture containers of the present technology can be untreated and uncoated, or optionally can be chemically or physically treated or coated to enhance cell adhesion. The cell culture containers disclosed herein can more easily and economically have large growth surfaces and/or complex or 3D surface shapes because no treatment or coating step is necessary. Further, the cell culture containers of the present technology can be environmentally degradable and suitable for composting in landfills.

A preferred thermoplastic resin for use in the present technology is a blend of poly-L-lactide resin (PLLA or PLA) and poly-D-lactide resin (PDLA or PDA). PLA can be commercially produced from agricultural biomass materials that provide plant starch, and PLA is considered environmentally sustainable. PLA is a polymer of L-lactate monomers, and both the polymer and monomer are enzymatically degraded and consumed by a variety of microorganisms. PDA is the enantiomer of PLA. PDA is a polymer of D-lactate monomers, which are produced by certain bacteria. Polymerization of D-lactate can produce PDA in various molecular weights.

Formula 1 depicts L-(+)-lactic acid, also known as (S)-lactic acid.

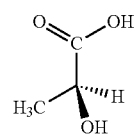

Formula 1

Formula 2 depicts D-(−)-lactic acid, also known as (R)-lactic acid.

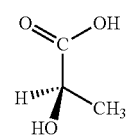

Formula 2

To allow visual and microscopic monitoring of cells as they are being cultured, the cell culture containers can be fully transparent at visible wavelengths of light. Unfortunately, transparent PLA (pure poly-L-lactide) has a low softening temperature (about 50° C.) that limits its use and would be inconsistent with most cell culture applications. The addition of microparticulate minerals such as talc and other substances is known to promote PLA crystallization, resulting in higher softening and melting temperatures. However, the resulting loss of transparency makes microparticle-modified PLA generally unsuitable for cell culture containers. Methods of admixing PDA resin with PLA resin disclosed herein can provide higher softening and melting temperatures while retaining transparency suitable for cell culture applications. Annealing methods are disclosed herein which can retain the transparency of a mixture of PLA and PDA, and the mixture can simultaneously have a softening temperature greater than 50° C.

A general structure of poly-lactide (or polylactide) is shown in Formula 3. In Formula 3, the methyl groups are each attached to a chiral center. Each chiral center can be the (S)-configuration or the (R)-configuration. When referring to a monomer of lactic acid (lactide), the (S)-configuration is (L) or levorotatory. PLA contains lactides in the (S)- configuration. By comparison, PDA contains lactides in the (R)-configuration which is (D) or dextrorotatory. In Formula 3, the methyl groups can assume either the (S) or (R) configuration, so the general structure of poly-lactide can comprise either enantiomer of lactic acid.

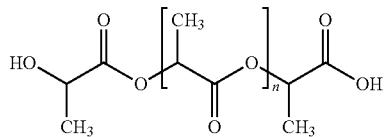

Formula 3

Depending on polymerization conditions, polymerization of either (R) or (S) lactic acid can result in polymers having different molecular weights. For example, a linear molecular formula of poly-lactide can be illustrated with $H(C_3H_4O_2)_nOCH_3$, $(C_3O_2H_4)_n$, $CH_3(C_3O_2H_4)_nCH_3$, or with $(C_3O_3H_5)$—$(C_3O_2H_4)_n$—$(C_3O_2H_5)$. In Formula 3, for example, with each monomer unit having a molecular mass of 72 g per mole, a value of "n" greater than 1500 can represent a polymer with molecular weight ($M_w$) greater than 100,000 Da. The value of n selected for polymerization and resin manufacture will depend upon the polylactide product application, where an extruded film may require an n of approximately 4,000 or a $M_w$ of ≈300,000 Da while an injection-molded container may require an n of approximately 1,400 or a $M_w$ of ≈100,000 Da. In general, the value of n can be at least 100, 200, 300, 500, 1000, 1400, 1500, 2000, 3000, 4000, or 5000 or more. Optionally coupled with any of these lower limits, as appropriate, the value of n can be less than or equal to 10000, 5000, 3000, 2000, 1500, 1200, 1000, or 500.

Polymerization of a racemic mixture of L- and D-lactides can lead to the synthesis of poly-DL-lactide (PDLLA) polymer, which can be amorphous. Depending on the ratio of enantiomers used during polymerization, different forms of PDLLA can be obtained. Poly(L-lactide-co-D,L-lactide) (PDLLA) is a thermoplastic aliphatic polyester synthesized from both enantiomers (D and L) of lactic acid. PDLLA has some monomers with alternating (R) and (S)-configuration, as shown in the example monomer 'm' of Formula 4. In monomer 'm' in Formula 4, the leftmost methyl group is in the (R) (or D) configuration, with the next methyl group in the (S) (or L) configuration. In general, the values of m and n each can be independently at least 100, 200, 300, 500, 1000, 1400, 1500, 2000, 3000, 4000, or 5000 or more. Optionally coupled with any of these lower limits, as appropriate, the value of m and n each can be independently less than or equal to 10000, 5000, 3000, 2000, 1500, 1200, 1000, or 500.

Different forms of poly-lactide, for example, comprising different repeating sequences of D and L in a poly-lactide polymer can yield materials with different degrees of crystallinity, thermal transitions, solubility, and rates of degradation.

Formula 4

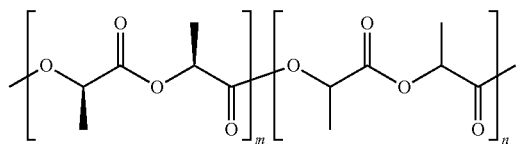

The present technology can comprise different forms of poly-lactide polymer. The molecular weights of the various poly-lactide polymers can vary. The present technology can utilize poly-lactide polymers with branching at any position, with branching upon branching, or without branching (straight chain polymers).

As used herein, "poly-L-lactide", "poly(L-lactide)", "PLA", or "PLLA" refers to a polymer consisting of (S)-lactic acid and does not refer to racemic PLLA (racemic poly-L-lactic acid). As used herein, "poly-D-lactide", "poly (D-lactide)", "PDA", or "PDLA" refers to a polymer consisting of (R)-lactic acid and does not refer to racemic PDLA (racemic poly-D-lactic acid). Branching can be introduced during polymerization of lactic acid, and both "poly-L-lactide" (PLA, PLLA) and "poly-D-lactide" (PDA, PDLA) can refer to branched or unbranched polymers of (S)-lactic acid or (R)-lactic acid, respectively. During synthesis of PLA, some (R)-lactic acid can be present, so throughout this technology, the PLA can have some impurity, (R)-lactic acid, in the polymer. Similarly, during synthesis of PDA, some (S)-lactic acid can be present, so throughout this technology, the PDA can have some impurity, (S)-lactic acid, in the polymer. Highly pure forms of PLA and PDA are desirable, but polymerization utilizing chiral monomers can contain some chiral impurity.

As used herein, a "mixture of D- and L-enantiomer polymers" of polylactide refers to a mixture of PLA and PDA polymers. For example, a mixture can be 95% (weight/weight) PLA and 5% (weight/weight) PDA, wherein the PLA and PDA are separate (non-joined) polymers. Another example of a mixed polymer is a single polymer chain containing 95% PLA and 5% PDA (w/w). Yet another example is a mixture of single polymer chain wherein 95% (weight) of the initial polymer units are PLA and 5% (weight) of the final polymer units are PDA. All mixtures of PLA and PDA of the present technology can contain 0-100% PDA and 0-100% PLA, with the total of PDA+PLA=100%.

As used herein "2D cell culture" refers to a culture of cells grown on a flat surface. The cells can be grown as a monolayer on Petri dishes, flasks, multi-well plates, or other cell culture containers. Additional cells optionally can grow over the initial monolayer, forming additional layers. "3D cell culture" refers to a culture of living cells inside or upon surfaces forming a 3D structure, such as a cell scaffold, which can mimic native tissue and organ specific microarchitecture. In 3D cell culture, growth of cells in a 3D arrangement can allow better cell-to-cell contact and intercellular signaling networks. The 3D cell culture can facilitate developmental processes allowing cells to differentiate into more complex structures. 3D cell culture can be described as organotypic culture, involving the growth of cells in a three-dimensional (3-D) environment. A 3D cell culture can be biochemically and physiologically more similar to in vivo tissue. In 3D cell culture, cells may be cultured and supported in three dimensions, e.g., on and around fibers, beads, sponges, lattices, matrices, or scaffolds.

The term "adherent cells" describes anchorage-dependent cells that are cultured on a suitable substrate that chemically and/or physically promotes cell adhesion and spreading. For culturing adherent cells and for growth of adherent cells, a cell culture container that the cells can attach to is required. Growth of adherent cells in a cell culture container typically begins with a monolayer of cells attached to or anchored to a growth surface of the cell culture container. The present technology can provide a suitable substrate for culture of adherent cells without any treatment or coating of the culture container. The majority of cells derived from vertebrates are adherent cells, with the exception of hematopoietic cell lines and certain others. Some adherent cell lines can also be adapted for suspension culture. Many commercially available insect cell lines grow well in monolayer or suspension culture.

Anchorage dependence refers to the need for cells to be adhered to or in contact with a solid surface or another layer of cells. Cells can be adhered to other cells or to extracellular matrix, for example. In cell culture containers that require a coating, cells can adhere to a coating of amino acids or protein affixed to a plastic surface of a conventional culture container. The coating of amino acids or protein can contain carbonyl groups. Adherent cells can be sensitive to an anchored state through physical cytoskeletal signaling, as well as through juxtacrine or gap/tight junction mediated signaling. Typically, epithelial cells are anchorage dependent and will die if no longer adhered to other cells, a process referred to as anoikis.

The term "biodegradable" refers to polymers that degrade fully (i.e., down to monomeric species) under long-term composting or other decomposition by bacteria or other living organisms, including fungi. Biodegradable polymers are not necessarily hydrolytically degradable and may require enzymatic action to fully degrade.

As used herein, a "cell culture container" can be a Petri dish, a culture flask, a roller bottle, a microwell or multiwell plate (e.g., 24-well, 96-well, 384-well plates), or any container suitable for cell culture. A "cell culture container" can have one or more 2D growth surfaces, and/or it can have 3D features for cell growth. The 3D features, for example, can be inserts, beads, lattices, micro-scaffolds, sponge-like structures, spheroids, web-like structures, and surfaces within multiple growth arenas for cell culture.

As used herein, the term "forced flow molding" refers to a method of forming a cell culture container or cell growth structure from a polylactide polymer resin melt at a temperature and pressure that allow the resin material to readily flow, and the polymer molecules within the resin material to readily become aligned in the direction of resin flow as adequate pressure is applied to the resin material, resulting in formation of the cell culture container or cell growth structure.

The term "compostable" means that a compound or material is capable of disintegrating into natural elements in a compost environment, leaving little or no toxicity in the resulting compost material. At least some beginning of composting typically occurs in about 90 days or less under ideal composting conditions. A compost environment can have organic matter such as dead leaves, twigs, grass clippings, vegetable waste, fruit scraps, coffee grounds, and moisture. The process of composting can involve making a heap of wet organic matter and waiting for the materials to break down into humus after a period of months.

As used herein, the term "electromagnetic radiation" can include radio waves, microwaves, infrared (IR), visible light, ultraviolet, high energy electrons or an electron beam, X-rays, and/or gamma rays.

As used herein, the term "enantiomer" refers to a molecule that is a mirror image of another; an "enantiomeric pair" is a pair of molecules that are mirror images of each other. An enantiomer can contain one or more chiral centers (stereocenters). A pair of enantiomers differs only in the spatial arrangement of their atoms, resulting in enantiomers being stereoisomers. Diastereomers are stereoisomers that are not mirror images of one another and are non-superimposable on one another. Stereoisomers with two or more chiral centers (stereocenters) can be diastereomers. As used herein, a poly-L-lactide polymer can be an enantiomer of a poly-D-lactide polymer. A poly-L-lactide polymer can be a diastereomer of a poly-D-lactide polymer if, for example, there are differences in purity of one or more chiral centers, differences in polymer chain length or branching, or differences in polymer secondary form. The polymer PDLLA is a diastereomer of poly-L-lactide and of poly-D-lactide.

The "heat deflection temperature" or "heat distortion temperature" (HDT, HDTUL, or DTUL) is the temperature at which a polymer or plastic sample deforms under a specified load. An example of a method to measure HDT is to expose a plastic to an elevated temperature in air and to observe whether distortion of the plastic occurs.

The term "hydrophilic," as used herein, refers to the property of having affinity for water. Compounds having hydrophilic properties can, for example, have hydrogen bond accepting functional groups, to which water can form hydrogen bonds. Hydrophilic polymers (or hydrophilic polymer segments) are polymers (or polymer segments) which can have affinity for aqueous solutions (i.e., are generally water soluble) and/or have a tendency to absorb water. In general, the more hydrophilic a polymer is, the more that polymer tends to be wetted by water. The term "hydrophobic," as used herein, refers to the property of lacking affinity for, or even repelling water.

For example, the more hydrophobic a polymer (or polymer segment), the more that polymer (or polymer segment) tends to not be wetted by water.

The kilogray is a derived metric (SI) measurement unit of absorbed radiation dose of ionizing radiation, e.g. high energy electrons, X-rays or gamma rays. One kilogray is equal to one thousand gray (1000Gy), and the gray is defined as the absorption of one joule of ionizing radiation by one kilogram (1 J/kg) of matter.

The term "microparticle" refers to any particle having at least one dimension on the microscale. The term "microscale" refers to a feature or structure having at least one dimension in the range from about 1 micron to about 1000 microns. The term "nanoscale" refers to a feature or structure having at least one dimension in the range from about 1 nm to about 999 nm.

The term polymer "molecular weight" can have different meanings. The term can refer to "average molecular weight" (Mi) that is the molecular weight as calculated by the weight of the molecule that is most prevalent in the mix that makes up a molecule. The term can alternatively refer to "number average molecular weight" (Mn), which is the molecular weight determined by counting the number of tall the different-sized molecules t in a mixture of polymer molecules and determining the weight, Mn, for which half the number of molecules in the mixture are larger and half are smaller than that Mn value. Or, the term can refer to "weight average molecular weight" (Mw), which is the molecular weight as calculated by taking all the different weight molecules in a mixture of polymer molecules and determining the weight, Mw, for which half the total weight of molecules is greater and half is less than that Mw value. The units for the molecular weight are typically Dalton (Da) or kilodalton (KDa, plural kilodaltons).

The dispersity (Đ) or polydispersity index (PDI) is a measure of the distribution of molecular mass in a given polymer sample. The Đ or PDI of a polymer is calculated as PDI=Mw/Mn, where Mw is the weight average molecular weight and Mn is the number average molecular weight. Mw is more sensitive to polymer molecules of high molecular weight, while Mn is more sensitive to polymer molecules of low molecular weight. The Đ or PDI of a polymer indicates the distribution of individual molecular weights in a collection or batch of polymers. The Đ or PDI has a value equal to or greater than 1, but as the polymers in a given batch approach the same chain length, the Đ or PDI approaches 1. A polymer material is denoted by the term disperse, or non-uniform, if its chain lengths vary over a wide range of molecular masses.

As used herein, the term "transparent" means allowing visible light to pass through, such that shapes and objects can be discerned or focused upon utilizing the light passing through, either without or with a light microscope, such as to discern cellular morphologies and cellular organelles. The term "translucent" means allowing light, but not details of shapes, to pass through.

As used herein, the term "untreated surface" refers to a surface of a cell culture container that has not been exposed to a treatment other than sterilization, or coated to improve cell adherence upon the surface. By comparison, various treatments and coatings are known to improve cell adherence upon a surface, and the treatments include a variety of physio-chemical processes such as microwave plasma oxygen gas treatment, poly-L-lysine or poly-D-lysine coatings or protein coatings applied to polystyrene container surfaces.

As used herein, the Vicat softening temperature (VST) is the temperature at which a standard indenter (a flat-ended needle with a 1 mm$^2$ circular or square cross-section) penetrates 1 mm into the surface of a plastic test specimen under a constant load when the temperature is increased at a uniform rate. For the "Vicat A test", a load of 10 N is used. For the "Vicat B test", the load is 50 N. A Vicat softening temperature can be utilized to measure a softening point for materials that have no definite melting point, such as polymers, plastics, and glasses.

As used herein, a plastic cell culture container "without surface modification" refers to a container whose surfaces substantially retain their structure, chemical properties, and physical properties as they existed after formation of the plastic container from a resin, and which have not been treated other than to a sterilization process as required for cell culture. Surface modification would include, for example, surface melting, abrasion, oxygen and/or nitrogen plasma treatment, chemical addition/modification, or coating addition, such as coating with one or more biomolecules such as proteins, peptides, nucleic acids, lipids, proteoglycans, or polysaccharides, or coated with a polymer not present in the body of the container. In some surface-modified cell culture containers, oxygen plasma microwave treatment adds oxygen to a polystyrene plastic surface, or protein, or polypeptide coatings including positively charged poly-L-lysine or poly-D-lysine of various molecular weights bind to a negatively charged plastic surface such as polystyrene and contain carbonyl groups or oxygen atoms that can extend from a charged plastic surface and interact with cells; such treatments or coatings are unnecessary and can be excluded in the present technology, wherein the cell culture container can be used for culturing adherent cells and non-adherent cells without substantial surface modification. The surfaces of cell culture containers of the present technology can allow mammalian cell adhesion and growth without the need for any specific surface modification.

The term "about" as used herein, generally refers to a particular numeric value that is within an acceptable error range as determined by one of ordinary skill in the art, which will depend in part on how the numeric value is measured or determined, i.e., the limitations of the measurement system. For example, "about" can mean a range of ±20%, ±10%, or ±5% of a given numeric value.

As used herein, the terms "highly pure" and "high purity" are defined as a material having a purity of about 95-100%, 96-100%, 97-100%, 98-100%, 99-100%, 99.9-100%, 99.99-100%, or 99.999%-100%. As used herein, "chirally pure" means about 95-100%, 96-100%, 97-100%, 98-100%, 99-100%, 99.9-100%, 99.99-100%, or 99.999%-100% of the (S) chiral centers in poly-L-lactide are (S) and of the (R) chiral centers in poly-D-lactide are (R), respectively. As such, chiral purity can be specified as at least 80%, at least 90%, at least 95%, at least 98%, at least 99%, and at least 99.5%.

The technology is further summarized by the following list of features.

1. A cell culture container comprising a mixture of polylactide polymers, the mixture comprising (100−X) wt % of poly-L-lactide and X wt % of poly-D-lactide, wherein X≤10, and wherein 100 wt % represents the total weight of polylactide polymers in the mixture.
2. The cell culture container of 1, wherein the material consists of (100−X) wt % of poly-L-lactide and X wt % of poly-D-lactide, wherein X≤10.
3. The cell culture container of any of 1-2, wherein X is from 0.5 to 10.
4. The cell culture container of 3, wherein X is from 0.5 to 5.
5. The cell culture container of any of 14 wherein the poly-L-lactide is at least 99% chirally pure; wherein the poly-D-lactide is at least 99% chirally pure; and wherein the poly-L-lactide and the poly-D-lactide are each at least 99% unbranched polymers.
6. The cell culture container of any of 1-5, wherein the material has a Vicat softening temperature greater than 60° C.
7. The cell culture container of any of 1-6, wherein the container is biodegradable.
8. The cell culture container of any of 1-7, wherein the container is compostable.
9. The cell culture container of any of 1-8, wherein the material is transparent.
10. The cell culture container of any of 1-9 that is viability-sustaining for a live culture of anchorage-dependent cells.
11. The cell culture container of 10, wherein >50% of cells in the culture remain ATP positive at 24 hours after cell seeding.
12. The cell culture container of any of 1-11 that is viability-sustaining for a live culture of suspension-growing cells, suspension-adapted cells, anchorage-dependent cells, and cells growing on a gelled culture medium.
13. The cell culture container of 12, wherein >50% of cells in the culture remain ATP positive at 24 hours after cell seeding.
14. The cell culture container of any of 1-13, wherein container is configured as a container selected from the group consisting of a Petri dish, a cell culture flask, a multi-well plate, and a roller bottle.
15. The cell culture container of any of 1-14, further comprising one or more anchorage-dependent cells attached to a growth surface in the container.
16. The cell culture container of any of 1-15, further comprising one or more suspension-dependent or suspension-adapted cells within a liquid culture medium in the container.
17. The cell culture container of any of 1-16, further comprising one or more cell growth structures selected from the group consisting of channels, lattices, matrices, webs, sponges, fibers, scaffolds, and beads; wherein said one or more cell growth structures comprise a mixture of polylactide polymers, the mixture comprising (100−X) wt % of poly-L-lactide and up to X wt % of poly-D-lactide, wherein X≤10, and wherein 100 wt % represents the total weight of polylactide polymers in the mixture.

18. The cell culture container of any of 1-17, wherein a cell growth surface of the container is devoid of any surface coating or chemical or physical surface modification.

19. A cell growth structure comprising a material comprising (100−X) wt % of poly-L-lactide and X wt % of poly-D-lactide, wherein X≤10.

20. The cell growth structure of 19, wherein X is from 0.25 to 10.

21. The cell growth structure of 20, wherein X is from 0.5 to 5.

22. The cell growth structure of any of 19-21, wherein the poly-L-lactide is at least 99% chirally pure; wherein the poly-D-lactide is at least 99% chirally pure; and wherein the poly-L-lactide and the poly-D-lactide are each at least 99% unbranched polymers.

23. The cell growth structure of any of 19-22 that is configured as a structure selected from the group consisting of channels, lattices, matrices, webs, sponges, fibers, scaffolds, and beads.

24. A method of making a cell culture container, the method comprising:
  (a) heating a mixture of polylactide polymers comprising (100−X) wt % of poly-L-lactide and X wt % of poly-D-lactide, wherein X≤10 to a molding temperature, and wherein 100 wt % represents the total weight of polylactide polymers in the mixture;
  (b) molding the mixture to form a structure having a shape of said cell culture container;
  (c) cooling the structure; and
  (d) optionally annealing the structure for an annealing time at an annealing temperature;
whereby said cell culture container is obtained.

25. The method of 24, wherein X is from 0.25 to 10.

26. The method of 25, wherein X is from 0.5 to 5.

27. The method of any of 24-26, wherein the poly-L-lactide is at least 99% chirally pure; wherein the poly-D-lactide is at least 99% chirally pure; and wherein the poly-L-lactide and the poly-D-lactide are each at least 99% unbranched polymers.

28. The method of any of 24-27, wherein annealing is performed, and the annealing time is from 20 seconds to 5 minutes.

29. The method of any of 24-28, wherein annealing is performed, and the annealing temperature is from 70° C. to 95° C.

30. The method of any of 24-29, wherein the molding comprises injection molding.

31. The method of any of 24-30, further comprising sterilizing the cell culture container.

32. The method of any of 24-31 that does not comprise applying a surface coating or chemically or physically modifying a surface of the container to enhance cell adhesion to the surface.

33. The method of any of 24-32, wherein the container is viability-sustaining for an anchorage-dependent cell type.

34. The method of any of 24-33, wherein the container is viability-sustaining for suspension-grown cells within a liquid culture medium in the container.

35. A method of culturing cells, the method comprising:
  (a) providing the cell culture container of claim 1;
  (b) adding cells and a culture medium to the container; and
  (c) incubating the container, cells, and culture medium for an incubation time and at an incubation temperature such that the cells are viably sustained and optionally reproduce.

36. The method of 35, further comprising after step (c):
  (d) allowing the container to be biodegraded and/or composted.

37. The method of any of 35-36, wherein the cells comprise an anchorage-dependent cell type.

37a. The method of any of 36-37, wherein the anchorage-dependent cell type adhere to a growth surface of the cell culture container, wherein said growth surface is devoid of any surface coating or chemical or physical surface modification.

38. A cell culture container consisting essentially of a polylactide polymer material, the material consisting of (100−X) wt % of poly-L-lactide and X wt % of poly-D-lactide, wherein X≤10, wherein 100 wt % represents the total weight of polylactide polymers in the material, and wherein the cell culture container is formed from the polymer material by a forced flow molding method and has been sterilized by gamma irradiation or electron beam irradiation, thereby increasing the hydrophilicity of a cell growth surface of the container compared to the cell growth surface without said irradiation.

39. The cell culture container of feature 38, wherein the forced flow molding method is selected from the group consisting of blow molding, rotational blow molding, injection blow molding, injection stretch blow molding, extrusion molding, extrusion molding followed by thermoforming, thin-wall injection molding, micro injection molding, and gas-assisted injection molding.

40. The cell culture container of any of features 38-39, wherein the container is biodegradable.

41. The cell culture container of any of features 38-40, wherein the container is compostable.

42. The cell culture container of any of features 38-41, wherein the material is transparent.

43. The cell culture container of any of features 38-42 that is viability-sustaining for a live culture of anchorage-dependent cells.

44. The cell culture container of any of features 38-43 that is viability-sustaining for a live culture of suspension-growing cells, suspension-adapted cells, anchorage-dependent cells, and cells growing on a gelled culture medium.

45. The cell culture container of any of features 38-44, wherein the container is configured as a container selected from the group consisting of a Petri dish, a cell culture flask, a multi-well plate, and a roller bottle.

46. The cell culture container of any of features 38-45, including one or more cell growth structures selected from the group consisting of channels, lattices, matrices, webs, sponges, fibers, scaffolds, and beads; wherein said one or more cell growth structures consist essentially of a polylactide polymer material, the material consisting essentially of (100−X) wt % of poly-L-lactide and up to X wt % of poly-D-lactide, wherein X≤10, and wherein 100 wt % represents the total weight of polylactide polymers in the mixture.

47. The cell culture container of any of features 38-46, wherein said cell growth surface of the container is devoid of any surface coating or chemical or physical surface modification other than by gamma irradiation or electron beam irradiation.

48. The cell culture container of any of features 38-47, wherein X=0.

49. The cell culture container of any of features 38-48, wherein said irradiation is at a dose in the range from about 25 kGy to about 55 kGy.

50. The cell culture container of any of features 38-49, wherein the increase in hydrophilicity is associated with an increase in tilt angle of a water droplet on said cell growth surface after said gamma irradiation or electron beam irradiation.

51. A cell growth structure consisting essentially of a polylactide polymer material consisting of (100–X) wt % of poly-L-lactide and X wt % of poly-D-lactide, wherein X≤10, and wherein the cell growth structure is formed by a forced flow molding method and has been sterilized by gamma irradiation or electron beam irradiation, thereby increasing the hydrophilicity of a cell growth surface of the cell growth structure compared to the cell growth surface without said irradiation.

52. The cell growth structure of feature 51, wherein the forced flow molding method is selected from the group consisting of blow molding, rotational blow molding, injection blow molding, injection stretch blow molding, extrusion molding, extrusion followed by thermoforming, thin-wall injection molding, micro injection molding, and gas-assisted injection molding.

53. A method of making a cell culture container, the method comprising:

(a) heating a polylactide polymer material consisting of (100–X) wt % of poly-L-lactide and X wt % of poly-D-lactide, wherein X≤10 to a molding temperature, and wherein 100 wt % represents the total weight of polylactide polymers in the mixture;

(b) subjecting the material to a molding method comprising forced flow molding to form a structure having a shape of said cell culture container;

(c) cooling the structure;

(d) optionally annealing the structure for an annealing time at an annealing temperature; and (e) sterilizing the container obtained from step (c) or step (d) with gamma irradiation or electron beam irradiation; whereby said cell culture container is obtained.

54. The method of feature 53, wherein the forced flow molding method is selected from the group consisting of blow molding, rotational blow molding, injection blow molding, injection stretch blow molding, extrusion molding, extrusion followed by thermoforming, thin-wall injection molding, micro injection molding, and gas-assisted injection molding.

55. A method of culturing cells, the method comprising:

(a) providing the cell culture container of feature 38;

(b) adding cells and a culture medium to the container; and (c) incubating the container, cells, and culture medium for an incubation time and at an incubation temperature such that the cells are viably sustained and optionally reproduce.

56. The method of feature 55, further comprising after step (c):

(d) allowing the container to be biodegraded and/or composted.

57. The method of feature 56, wherein the cells comprise an anchorage-dependent cell type, and wherein the anchorage-dependent cell type adheres to said growth surface of the cell culture container, wherein said growth surface is devoid of any surface coating or chemical or physical surface modification other than by gamma irradiation or electron beam irradiation.

BRIEF DESCRIPTION OF THE DRAWINGS

FIG. 1 shows a schematic representation of an embodiment of a method of making a transparent cell culture container with 2D and/or 3D growth surfaces.

DETAILED DESCRIPTION

The present technology provides cell culture containers made from blends of poly-L-lactide (PLA) and poly-D-lactide (PDA) which blends are transparent, have good temperature and mechanical stability, and are biodegradable and compostable. These cell culture containers also can provide excellent anchorage for adherent cells without any cell adhesion-promoting coating or surface treatment.

PLA is a readily biodegradable polymer which has been used to produce a variety of plastic consumer articles, typically by injection molding at temperatures in the range from about 178° C. to about 240° C. PLA has a melting temperature in the range from about 157° C. to about 170° C. However, molded products made from PLA have a heat deflection temperature from about 49° C. to about 52° C., and their Vicat softening temperature is about 50° C. This makes pure PLA unsuitable for making cell culture containers, as the containers would deform at temperatures greater than about 50° C. The present inventor has discovered that suitable cell culture containers with highly desirable properties of heat stability, transparency, biodegradability, and compatibility with adherent cells can be made by combining PLA with PDA to form a polymer blend before molding.

Enantiomers generally have similar chemical properties, except when they interact with other chiral compounds or with some enzymes. Thus, the melting temperature, heat deflection temperature, and Vicat softening temperature of a sample of PDA will be the same as a sample of PLA if their polymer MW and branching are the same. Surprisingly, by mixing certain proportions of PDA with PLA, it is possible to form cell culture containers with a high tolerance for heat. The cell culture container can be transparent and can be compostable. Unexpectedly, such cell culture containers can be used with adherent cells without the need for chemical or physical treatments or applying adhesion-promoting coatings.

PLA and PDA polymers for use in the present technology can be of any molecular weight useful to produce suitable cell culture containers. For example, the molecular weight can be a value specified as suitable by the resin manufacturer for manufacturing containers by injection molding, blow-molding, or thermoforming. For an injection-molding resin, a typical polylactide molecular weight can be about 100,000 Da or from about 75,000 to 125,000 Da, or from about 50,000 to 150,000 Da. for example. The polymers have any dispersity (Ð) and any level of polymer branching consistent with the desired properties of suitability for manufacturing and use as a cell culture container, or desired values of Vicat softening temperature, transparency, biodegradability, and/or cell attachment.

The PLA and PDA polymers utilized to form cell culture containers herein can have various substituents on various methyl groups or various carbonyl groups. For example, Formula 5 illustrates substituents R1, R2, and R3 on methyl groups in PLA, PDA, or a diastereomer of PLA or PDA. In general, the value of n can be at least 100, 200, 300, 500, 1000, 1400, 1500, 2000, 3000, 4000, or 5000 or more. Optionally coupled with any of these lower limits, as appropriate, the value of n can be less than or equal to 10000, 5000, 3000, 2000, 1500, 1200, 1000, or 500.

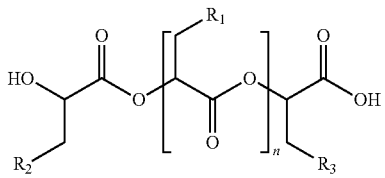

Formula 5

Formula 6 illustrates substituents R4, R5, and R6 on the carbonyl oxygens of PLA, PDA, or a diastereomer of PLA or PDA. In general, the value of n can be at least 100, 200, 300, 500, 1000, 1400, 1500, 2000, 3000, 4000, or 5000 or more. Optionally coupled with any of these lower limits, as appropriate, the value of n can be less than or equal to 10000, 5000, 3000, 2000, 1500, 1200, 1000, or 500.

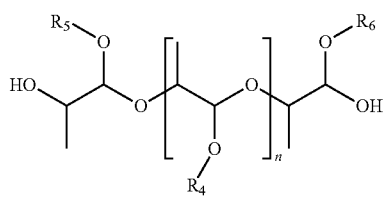

Formula 6

The substituents R1, R2, R3, R4, R5, and R6 (R1-R6) in Formulas 5 and 6 can be independently selected and can all be the same or different. Substituents on methyl groups, for example in Formula 5, can be present (or combined) with substituents on carbonyl groups, for example in Formula 6. The substituents R1, R2, and R3 (R1-R3) can be present but without any substituents R4, R5, and R6 (R4-R6) on carbonyls. R1-R3 can be hydrogen and R4-R6 can be no substituents. For example, R1-R3 can be hydrogen, hydroxy, sulfoxy, halo, acyl, acyloxy, alkyl, heteroalkyl, alkenyl, heteroalkenyl, alkynyl, heteroalkynyl, alkoxy, cycloalkyl, heterocycloalkyl, aryl, arylalkyl, arylhalo, arylhydroxy, arylcyano, aryltrifluoromethyl, aryltrifluoromethoxy, arylnitro, aryltrifluoro-methoxy, aryl ether, aryl ester, aryl sulfonyl, aryl sulfinyl, aryl sulfonamidyl, aryl sulfonate, aryl sulfoxyl, aryl phosphate ester, aryl carbonyl, aryl carboxylate, aryl carbamate, aryl amine, aryl imide, heteroaryl, heteroarylalkyl, heteroarylhalo, heteroarylhydroxy, heteroarylcyano, hetero-aryltrifluoromethyl, aryltrifluoromethoxy, arylnitro, heteroaryltrifluoromethoxy, heteroarylnitro, heteroarylether, heteroarylester, heteroarylsulfonyl, heteroarylsulfinyl, heteroarylsulfonamidyl, heteroarylsulfonate, heteroarylsulfoxyl, heteroarylphosphate ester, heteroarylcarbonyl, heteroarylcarboxylate, heteroarylcarbamate, heteroarylamine, heteroarylimide, quinidine, morpholine; any ring structure can be optionally substituted with any of the substituents described herein; and any two adjacent substituents can come together to form a carbocyclic or heterocyclic ring system. The substituents R4-R6 can include any the aforementioned substituents for R1-R3 that are suitable for covalent attachment to oxygen.

The PLA or PDA polymers utilized in the present technology can be neutral or can have positive or negative charges on various substituents (e.g., protonated tertiary amino groups or deprotonated carboxyl groups). The PLA and PDA can have negative charge on one or more oxygen atoms as is shown in Formula 7, where associated cations A+, B+, and D+ can be the same or different. A+, B+, and D+ can have multivalent charge and can form salts with the polylactide polymer chain in hemi, mono, bis, and other configurations. The negative charge on an oxygen illustrated in Formula 7 can be a partial charge, as resonant structures are possible with a carbonyl adjacent to O—, further illustrating the possibility for hemi, mono, bis, and other salt configurations.

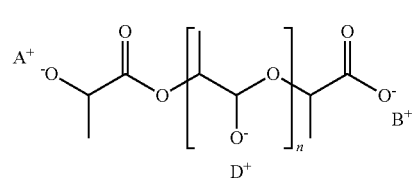

Formula 7

A+, B+, and D+ can be independently organic or inorganic cations, a trivalent metal cation, or a monovalent alkali earth metal cation. In Formula 7, the D+ cation can be absent and the negatively charged oxygen associated with D+ can be a carbonyl, such that A+ and B+ form salts without presence of D+. Although not illustrated in Formula 7, organic anions, for example a borate, can interact with various functional groups either covalently attached to the polylactides or to cations in ionic attachment to the polylactides.

The PLA and the PDA utilized to form cell culture containers can have various, independently selected, functional groups on the terminal ends of the PLA and the PDA. Functional groups on the terminal ends are various functional groups that can be covalently attached to the terminal ends of a main polymer backbone (chain) of PLA or PDA and to terminal ends of branching polymer chains extending from the main polymer backbone, or from other branching polymer chains. Formula 8 represents a non-limiting example of an amine functional group attached to a terminal end of PLA.

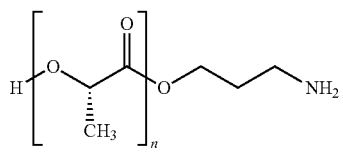

Formula 8

The amine functional group illustrated in Formula 8 can represent any other suitable functional group for attachment to terminal ends of PLA or PDA. Non-limiting examples of functional groups are esters, thiols, propargyl (from alkyne propyne), azide, acrylate, methacrylate, or N-2-hydroxyethylmaleimide. The functional groups attached to terminal ends can form bridges between or among polymer chains.

The PLA and the PDA utilized to form cell culture containers can have independently selected, joining functional groups on the terminal ends of the PLA and the PDA. Joining functional groups can attach to one or more terminal ends of PLA or PDA and join the PLA or PDA to other polymers of PLA or PDA. In this way, one or more joining functional groups can extend the polymer length of PLA or PDA. Any joining group suitable for attachment to PLA or PDA, with further attachment to PLA or PDA can be utilized. A non-limiting example is a secondary amine that is attached to a PLA polymer on both ends. For example, the primary amine illustrated in Formula 8 can be a secondary amine with PLA polymers attached on both sides of the secondary amine.

Addition of compounds, salts, or chemicals to PLA can increase the Vicat softening temperature and the heat deflection temperature, but can result in a loss of transparency. For example, the addition of talc to PLA can be utilized to produce opaque cutlery and dishware that can have tolerance for temperatures over 50° C. The present cell culture containers can contain additional materials other than PLA and PDA. If materials other than PLA and PDA are added, materials and/or their amounts preferably are selected such that the transparency of the resulting cell culture containers is maintained. For example, PEG (polyethylene glycol), PPG (polypropylene glycol), or other plasticizers can be added. Releasing agents, coloring agents, and/or crystallization agents can be added. Optionally, compounds can be added to improve transparency or to filter or block total transmission of ranges of the electromagnetic spectrum, such as to provide color or to protect cells within the container from certain wavelengths of electromagnetic radiation. Optionally, micro or nanoparticles can be added, for example, to block or partially filter UV light.

Surface coatings such as poly-D-lysine, collagen, antibodies, or aptamers can optionally be added to the cell culture containers to enhance cell adhesion or selectively adhere certain desired cell types. For example, addition of carbonyl groups or addition of oxygen atoms to a growth surface of a cell culture container can improve cell adhesion, and the oxygen atoms can act as hydrogen bond acceptors. While not intending to limit the technology to any particular mechanism, the mixtures of PLA and PDA disclosed herein can be used to form cell culture containers can produce surfaces having exposed carbonyl groups or oxygen atoms without the need for any treatment or coating step. The exposed carbonyl groups or oxygen optionally can be combined with other functional groups. Such exposed carbonyl groups or oxygen atoms can increase the hydrophilicity of a surface.

The present technology provides a method to produce cell adhesive, compostable (biodegradable), and transparent, cell culture containers. The method can comprise mixing PLA with a selected percentage (weight/weight) of PDA. The percentage of PDA can be, for example, about 0.5% to 50%, 1% to 50%, about 2% to 50%, about 2% to 30%, about 2% to 20%, about 2% to 10%, about 2% to 5%, about 1% to 20%, about 1% to 10%, about 1% to 5%, about 3% to 20%, about 3% to 10% about 4% to 20%, about 4% to 10%, about 5% to 20%, or about 5% to 10% by weight. Different mixtures or ranges of PDA content can be chosen depending on the intended use of the containers. For example, while 50% PDA can yield a higher Vicat softening temperature than a lower percentage, the use of 50% PDA also can increase the cost of a cell culture container. As another example, 1.0% PDA can enable a cell culture container to withstand temperatures of 70° C. water (see Example 1), but for some applications 5% PDA can be used so as to provide still higher thermal stability (>70° C.). Blends containing as little as 0.5% PDA, if used with annealing, can yield a cell culture container capable of withstanding 70° C. water.

The Mn or "number average molecular weight" of the PLA and the PDA utilized herein can be greater than about 1 KDa, greater than about 5 KDa, greater than about 10 KDa, greater than about 20 KDa, greater than about 30 KDa, greater than about 40 KDa, greater than about 50 KDa, greater than about 60 KDa, greater than about 70 KDa, greater than about 80 KDa, greater than about 90 KDa, greater than about 100 KDa, greater than about 200 KDa, greater than about 300 KDa, greater than about 400 KDa, and greater than about 500 KDa.

The Mw or "weight average molecular weight" of the PLA and the PDA utilized herein can be greater than about 2 KDa, greater than about 10 KDa, greater than about 20 KDa, greater than about 40 KDa, greater than about 60 KDa, greater than about 80 KDa, greater than about 100 KDa, greater than about 120 KDa, greater than about 140 KDa, greater than about 160 KDa, greater than about 180 KDa, greater than about 200 KDa, greater than about 300 KDa, greater than about 400 KDa, greater than about 500 KDa, greater than about 600 KDa, greater than about 700 KDa, greater than about 800 KDa, greater than about 900 KDa, and greater than about 1000 KDa.

The PLA and the PDA utilized herein can have high chiral purity such that greater than 95% of the (S) chiral centers are (S) or greater than 95% of the (R) chiral centers are (R), greater than 98% of the (S) chiral centers are (S) or greater than 98% of the (R) chiral centers are (R), and greater than 99% of the (S) chiral centers are (S) or greater than 99% of the (R) chiral centers are (R), respectively.

A method to produce a cell adhesive, compostable (biodegradable), and transparent, cell culture container can consist essentially of mixing PLA (100−X) % with a percentage (weight/weight) of PDA (X %). While the PLA and PDA are essential, other ingredients can be added that do not cause lack of transparency in a selected range from between about 380 to about 760 nm. Other ingredients can be added that do not make the mixture non-biodegradable. Other ingredients can be added that do not make the final cell culture container non-adherent to adherent cells. To consist essentially of can mean other ingredients (besides PLA and PDA) added do not cause lack of transparency, lack of biodegradability, or lack of cell adhesion in a cell culture container. To consist essentially of can mean that a suitable cell culture container is produced with viable adhesion for adhesive cells. A method to produce a cell adhesive, compostable (biodegradable), and transparent, cell culture container can consist of mixing PLA (100−X) % with a percentage (weight/weight) of PDA (X %). The percentage of PDA mixed with PLA can be selected from the range between 0.1% and 50% (weight/weight).

An example of a method to produce a cell culture container is shown in FIG. 1. The mixing of PLA and PDA, shown as 101, can be performed utilizing a mixture comprising PLA at (100−X) % (weight/weight) and PDA at X % (weight/weight), where 100% corresponds to the total amount by weight of PLA+PDA in the mixture. The percent of X can be from 0.1% to 50%. The mixing in 101 can be performed by any means known in the art, for example, tumbling, wet milling, dry milling, homogenization, sonic (or acoustic, resonant) mixing, and suspension mixing. The mixing in 101 can further comprise a drying step or any step to complete the mixing. A drying step can be to reduce moisture in the mixture before attempting a melting. A mixing step can be followed by, or can include, one or more drying steps for any purpose. A drying step is not limited in temperature or in vacuum conditions. For example, a drying step can employ a temperature from about 50° C. to 100° C., about 60° C. to 90° C., or about 70° C. to 80° C.

The mixture can then be heated to a molding temperature in 102 using any means known in the art. The molding temperature is not limited. For example, a molding temperature can be selected from about 100° C. to 600° C., about 125° C. to 300° C., about 150° C. to 275° C., or about 175° C. to 250° C.

After heating to a molding temperature, any of several types of forced flow molding methods, including injection molding, blow molding, rotational blow molding, injection blow molding, injection stretch blow molding, extrusion molding, and extrusion followed by thermoforming, can be utilized to shape a cell culture container. Injection molding can include high pressure injection of a mixture at or near a molding temperature. High pressure injection of a mixture of PLA and PDA, or PLA alone, can be utilized to form intricate parts or dimensions of larger components at or near the micrometer or nanometer scale. Other forms of injection molding that can be used include thin-wall injection molding, micro injection molding, gas-assisted injection molding, 3D printing can be utilized to mold, shape, or deposit a mixture of PLA and PDA into intricate parts or dimensions, and is particularly useful for making a small number of containers having a complex structure. Other types of molding such as blow molding, rotational blow molding, injection blow molding, injection stretch blow molding, extrusion molding, and extrusion followed by thermoforming can be used, and it is preferred that such methods involve introduction of resin under pressure, and such treatment is expected to align the polymer chains and result in dense packing of the chains, which is associated with an advantageous increase in hydrophilicity upon irradiation by gamma irradiation or electron beam irradiation.

Injection molding, or any suitable type of formation or shaping as described above, can occur at 103 wherein a shape of a cell culture container is formed from the mixture 101 at a molding temperature (102). The shape of the cell culture containers disclosed herein is not limited in any way, and the shape 105 can be a Petri dish, a culture flask, a roller bottle, a microwell or multiwell plate (e.g., 24-well, 96-well, 384-well plates), and any dish or container suitable for cell culture. 3D features can be separately molded; the 3D features, for example, can be inserts, beads (106), lattices, micro-scaffolds, sponge-like structures, spheroids, web-like structures, and surfaces with multiple growth arenas for cell culture. After the formation or shaping a cooling step can be performed at 103 to cool the shaped mixture such that the molded shape is retained.

Cooling can be to any temperature suitable to stabilize a shape of the container or a component thereof.

After injection molding, 3D printing, formation, or shaping at 103, an annealing step can be performed at 104. Annealing can improve the thermal stability of a cell culture container and can impart a crystallinity into the material which can improve thermal stability. Annealing generally refers to exposing the molded part to an selected temperature for a selected period of time, and can be carried out by any known process, such as tunnel annealing, oven annealing, heat lamp (infra-red) annealing, microwave annealing, radiation annealing, hot water bath annealing, hot air annealing, vacuum annealing, or sonic annealing. The annealing time can be about 1 to 15 minutes at a temperature in the range from about 20-75° C., or can be about 20 seconds or more, such as 20-60 seconds, at 90° C. Annealing time and temperature can be varied depending on, for example, the percentage of PDA in mixture 101 (higher levels of PDA enhance the annealing process), the desired Vicat softening temperature, the heat deflection temperature of products 105, 106, the thickness or shape of the product, or the desired optical clarity of the product (excessive annealing reduces optical clarity). Annealing time and temperature also can be varied due to humidity conditions, properties of the mixture, additives other than PLA and PDA in the mixture, and desired crystal forms. Further, annealing time and temperature can be varied based upon the molecular weights of the PLA and the PDA polymers. If a sufficiently high annealing temperature is used, the time of annealing can be shortened such that annealing takes place within the mold, and no separate annealing process is required. See, for example, Product Data Sheet for LUMINY D070 from Total Corbion PLA BV, Revision 7 May 2019, which is hereby incorporated by reference. It is within the routine skill in the art of plastics molding to routinely determine optimum annealing conditions for each molded part and polymer resin. In the present technology, the following parameters offer the best control over the annealing conditions: amount of PDA in the PLA/PDA mix, annealing temperature, and annealing time. The annealing conditions should be adjusted so as to obtain the desired heat stability of the part (e.g., as measured by Vicat softening temperature or other parameters) and optical clarity (for compatibility with light microscopy). Without intending to limit the technology to any particular mechanism, the annealing conditions are believed to impact the crystalline state of the polymers, which determine the heat stability and optical properties.

A lid 107 can optionally be made from mixture 101. The lid 107 shown in FIG. 1 can be formed by 101, 102, 103, 104, for example. Lid 107 and container 105 can comprise, for example, inserts, extensions, rods, lattices, dividers, well, observation areas, and notches, threads, or grooves for fastening lid 107 to container 105. The container 105, the 3D spheroids or beads 106, and lid 107 shown in FIG. 1 can form a unit, which can be stackable, which can interlock with adjacent units, or which can be combined with other units to form a larger 3D cell culture container. Optionally, container 105 can form a unit alone. Lid 107 can be formed from an entirely different material than the body of the cell culture container, particularly if no cell growth is desired on the lid.

Annealing can increase or cause a crystallization of the mixture comprising PLA and PDA. The crystallization can increase the heat tolerance of a cell culture container, for example, increasing the Vicat softening temperature or the heat deflection temperature. Annealing can be done at a time or a temperature that does not destroy the transparency of a cell culture container. For example, transparency can be halted when one or more crystal forms initiate change to a different crystal form. Annealing can cause a glass transition. Optionally, annealing can cause a transition to an amorphous form. Annealing can be performed in the injection mold or in the shaping of the cell culture container. Annealing can be performed after sterilization.

The cell culture containers disclosed herein can have a Vicat softening temperature or a heat deflection temperature greater than about 50° C., greater than about 60° C., greater than about 70° C., greater than about 80° C., greater than about 90° C., greater than about 100° C., greater than about 110° C., greater than about 120° C., and greater than about 130° C. Thermal stability of the cell culture containers disclosed herein can be measured by incubating the cell culture containers in air for 30 minutes at a testing temperature and by observing whether any visible warping of a flat bottom of the cell culture containers occurs. Thermal stability of the cell culture containers disclosed herein can be greater than about 60° C., greater than about 65° C., greater than about 70° C., greater than about 75° C., greater than about 80° C., greater than about 85° C., greater than about 90° C., greater than about 95° C., greater than about 100° C., greater than about 110° C., greater than about 120° C., and greater than about 130° C.

A growth surface area of a cell culture container can be larger than about 1 mm$^2$, larger than about 1 cm$^2$, larger than about 5 cm$^2$, than about 50 cm$^2$, larger than about 100 cm$^2$, larger than about 1 m$^2$, larger than about 5 m$^2$, or larger than about 10 m$^2$. The cell culture containers disclosed herein can have 3D features causing a large growth surface area to volume ratio in the cell culture containers. Growth surface area to volume can be measured by dividing growth surface area by volume. For example, 8 cm$^2$ divided by 2 cm$^3$=4 cm$^{-1}$. The growth surface area to volume ratio of the cell culture containers disclosed herein can have any desired value, or can be at least about 0.1 cm$^{-1}$, at least about 0.5 cm$^{-1}$, at least about 1 cm$^{-1}$, at least about 5 cm$^{-1}$, at least about 10 cm$^{-1}$, at least about 25 cm$^{-1}$, at least about 50 cm$^{-1}$, or at least about 100 cm$^{-1}$.

The cell culture containers disclosed herein preferably can contain hot water or hot aqueous solutions without deforming. For example, hot water can be poured into the cell culture containers without deformation of the cell culture containers. Optionally, the cell culture containers disclosed herein can withstand, without deformation, hot water at a temperature greater than about 70° C., greater than about 75° C., greater than about 80° C., greater than about 85° C., greater than about 90° C., greater than about 95° C., or greater than about 100° C. Optionally, agar can be gelled in a cell culture container disclosed herein without deforming the container.

The cell culture containers disclosed herein can be transparent. Transparency can be measured by total transmittance. For example, total transmittance can equal incident light minus (absorption+reflection). Optionally, the total transmittance of the cell culture containers disclosed herein can be greater than 10%, greater than 20%, greater than 30%, greater than 40%, greater than 50%, greater than 60%, greater than 70%, greater than 80%, or greater than 90%. Transparency can indicate lack of components or crystal forms with different indices of refraction. Transparency can be measured in one or more ranges or in one or narrow bands in the visible light spectrum from about 380 or 400 nm to about 700, 740, or 760 nanometers. Certain ranges between about 380 to about 760 nanometers can be made non-transparent for specific cell cultures, for example, by coatings, additives, or treatments (e.g., annealing). Coatings, additives, or treatments (e.g., annealing) can be applied to block or to inhibit electromagnetic waves in any desired range of the spectrum of electromagnetic radiation. If only one or more selected wavelength ranges are blocked, the cell culture container is still generally considered to be transparent. Particulates can be added to the mixture of PLA and PDA during mixing or after mixing. The particulates can be utilized, for example, for heat (IR) or UV absorption, and the particles may lower total transmittance while allowing transparency in one or more ranges between 380 to about 760 nm.

The cell culture containers can be sterilized after annealing. Optionally, sterilization can be accomplished by annealing or by a sterile manufacturing technique. Sterilization can be performed by any means known in the art, such as gamma irradiation or irradiation by a particle beam or electron beam.

The cell culture containers disclosed herein can be manufactured by mixing about 0.1% to about 50% PDA with PLA, melting the mixture to a suitable molding temperature, molding the melted mixture, cooling to a suitable release temperature, and then annealing the cell culture container. If pure PLA and PDA are utilized, the cell culture containers can comprise carbonyl groups extending from the PLA and PDA on the outer surfaces. The carbonyl groups can act as hydrogen bond acceptors. The cell culture containers can retain a water droplet, about 100 microliters in volume, without movement of the water droplet, at an angle in non-limiting examples, from about 0°-75°, about 0°-65°, about 0°-45°, about 0°-35°, about 0°-25°, about 0°-20°, about 0°-17°, about 0°-15°, and about 0°-12°. Electron beam irradiation (e.g., 25 kGy, 45 kGy, 55 kGy) can increase the hydrophilicity.

The cell culture containers disclosed herein can be utilized for culture of either suspension or suspension-adapted cell types or for anchorage-dependent/adherent cell types, eukaryotic cells, and prokaryotic cells. In the cell culture containers disclosed herein, bacterial *E. Coli* can be grown in any suitable medium. Luria Broth bacterial growth medium (1% tryptone, 1% NaCl, and 0.5% yeast extract in water) with 2% dissolved agar is a non-limiting example of a suitable medium. Yeast cells can be grown in the cell culture containers disclosed herein.

Surprisingly, the technology disclosed herein can provide cell culture containers for adherent cells without surface treatment or coating. The cell culture containers provided herein also can be used for cells that grow in suspension, or that grow both in suspension and attached to a surface or to other cells. The containers can be used for culturing cells derived from multicellular eukaryotes, animal cells, such as mammalian cells, including human cells, plant tissue or cell culture, fungal culture, and microbiological culture. Viral culture can be accomplished, for example, in the eukaryotic cells grown in the containers. For growth upon untreated and uncoated surfaces, any suitable growth or culture medium can be used. An example of a growth medium for eukaryotic cell growth is DMEM medium (Dulbecco's Modified Eagles Medium) supplemented with 10% fetal bovine serum, 2 mM L-glutamine, and 100 I.U./ml each of penicillin and streptomycin. The container can be placed in a 37° C. incubator with an atmosphere of 5% CO$_2$ in air. Because the growth surfaces of the containers provided herein do not necessitate treatment or coating before cultivation or growth, large surface area growth surfaces, 3D growth surfaces, and intricate growth surfaces can readily be produced more conveniently and at less cost than containers requiring surface treatment or coating.

Cell culture containers according to the present technology can sustain the viability of cells cultured therein. Both suspension-growing or suspension-adapted and anchorage-dependent cells can be viably sustained by containers of the present technology, as well as cells such as bacteria, yeast, or other fungi which grow on gelled culture medium. The viability sustaining feature of the containers can be assayed by any of a variety of known methods. For example, see promega.com/resources/guides/cell-biology/cell-viability/. Cell viability can vary depending on the cell species, seeding density, age of the cell culture following seeding, and other factors.

Cell culture containers of the present technology can be assessed, for example, by determining the fraction of cells that are measured as ATP positive. Cell culture containers of the present technology can be viability sustaining, for example, in that they maintain greater than 50%, or greater than 60%, or greater than 70%, or greater than 80%, or greater than 90% of cells in the culture as ATP positive at 24 hours after seeding the culture.

The technology described herein can provide cell culture containers of any size or shape for cell cultivation. The transparent cell culture containers disclosed herein and the methods disclosed herein can be utilized for cultivation, growth, sustenance, or multiplication of bacteria, Archaea (e.g, prokaryotes), Protozoa, Chromista (e.g., algae), plants, fungi, animal cells, viruses, or prions. The cell culture containers can be utilized for replication of DNA, RNA, amyloids, oligonucleotides, and polypeptides. For detaching adherent cells, the cell culture containers can be used with any detachment method known in the art, for example, by introducing trypsin into the container. Because the cell culture containers of the present technology are highly versatile, in that they can be utilized to culture a wide variety of different cell types, including anchorage-dependent cells, cells growing in suspension, cells adapted to growing in suspension, and cells growing on gelled media, the use of these cell culture containers can reduce the size, complexity, and cost of inventory for a research or cell production facility.

The technology described herein can be produced using 3D printing. For example, a mixture comprising poly-L-lactide at (100–X) % (weight/weight) and poly-D-lactide at X % (weight/weight), wherein X % is 0.1% to 50%, is introduced into a 3D printer. The heating element of the 3D printer can heat the mixture to a molding temperature. The robotic or moving printing head of the 3D printer can mold the mixture in the shape of a cell culture container (or almost any shape). The shaped or formed mixture can be cooled. The shaped or formed mixture can be annealed to form a transparent cell culture container, a 3D structure such as a cell scaffold for adherent cell culture and growth.

EXAMPLES

Example 1: Manufacture of Petri Dishes

Poly-D-lactide (PDA) was mixed with poly-L-lactide (PLA) in various percentages, molded, annealed, and tested to determine the ability to fill a Petri dish with water up to temperatures of 70° C. with no visible deformation in the product. Petri dishes were molded by EcNow Tech Inc. (34080 ExCor Road, Albany, Oreg. 97321). Four batches were made by combining PDA and PLA by weight percentages. Batch 1 was a control batch made of 100% PLA. Batch 2 was made up of 99.5% PLA and 0.5% PDA. Batch 3 was made up of 99.0% PLA and 1.0% PDA. Batch 4 was made up of 95% PLA and 5% PDA.

Materials were mixed in a tumble mixer for approximately ten minutes per batch. 21 Kg batches were used for each mixture. Each batch was dried at 170° F. (76.7° C.) for 6 hours per batch. Each batch was processed on an 85-ton Engel injection molding machine using a single cavity Petri dish tool. A hot tip was utilized for direct injection of plastic into the tool. The material was processed after drying at a melt temperature of 400° F. (204.4° C.). Post molding, the products were annealed by passing through a heat tunnel (oven) at 150° F. (65.6° C.) for 5, 10, or 15 minutes to impart crystallinity into the material. It was found that a 5 to 10-minute dwell time in the oven was sufficient to impart sufficient crystallinity without negatively impacting the transparency or clarity of the material. Testing of batches with hot water (70° C.) was conducted. The testing proved that 0.5% (w/w) of PDA in Batch 2 was sufficient with proper annealing (5-10 minutes) to enable the product to withstand temperatures of 70° C. when water at that temperature was poured into the Petri dishes.

Injection-molded PLA cell culture containers are typically transparent with a slightly yellowish cast that does not compromise their use. However, for esthetic purposes the yellowish cast can be corrected by adding a very small amount of optical brightener. Accordingly, one such optical brightener chemical, a bis(benzoxazol)stilbene compound was commercially obtained from the Sukano Polymers Corp. (Duncan, S.C.) already pre-diluted and dispersed in PLA (mixture known as PLA ob S515-N). This product was further diluted approximately 100-fold into the PLA-PDA resin blends and used to prepare injection-molded cell culture containers. Accordingly, the final concentration of optical brightener compound in the cell culture container molded parts was typically about 5-20 ppm, and substantially less than 100 ppm.

Example 2: Water Droplet Movement on 99% PLA with 1% PDA Petri Dishes

Petri dishes were molded by EcNow Tech Inc. by blending about 1% poly-D-lactide polymer with 99% poly-L-lactide polymer (weight/weight) as described in Example 1. Before testing, each Petri dish was washed with distilled water. An X marking was placed on the outside of each dish near its center. The X marking was used to monitor initiation of movement of a water droplet placed above that marking after tilting each Petri dish at increasingly steep angles.

Droplets of increasing micropipette-measured volumes (25, 50, and 100 microliters) of double-distilled water were applied to the bottom inside surface of each Petri dish, with the X marking on the outside of the Petri dish. Three droplets of each volume were tested on each Petri dish. Two non-irradiated Petri dishes were tested, and two Petri dishes were tested for each irradiated condition. The tilt angle for a Petri dish was set and measured using a protractor goniometer. Tables 2-4 summarize results for irradiated Petri dishes. Table 1 summarizes results for non-irradiated Petri dishes, and the measured elevation angle (using the protractor goniometer) is shown in degrees for each Petri dish and each droplet.

TABLE 1

Droplet Results for Two Non-Irradiated Petri Dishes.

| Water Droplet Size (microLiters): | Dish 1, Droplets 1, 2, 3 (Degrees) | Dish 2, Droplets 1, 2, 3 (Degrees) |
|---|---|---|
| 25 | 17.5, 17, 17 | 18.5, 18, 17.5 |
| 50 | 11, 11, 10.5 | 10, 11, 10.5 |
| 100 | 7.5, 8, 7.5 | 6, 6.5, 6 |

TABLE 2

Droplet Results for Two 25 kGy Electron Beam Irradiated Petri Dishes.

| Water Droplet Size (microLiters): | Dish 1, Droplets 1, 2, 3 (Degrees) | Dish 2, Droplets 1, 2, 3 (Degrees) |
|---|---|---|
| 25 | 26, 27.5, 27 | 28, 28.5, 27 |
| 50 | 13, 14, 13 | 16, 15, 16 |
| 100 | 8, 8.5, 8 | 11, 11.5, 11.5 |

TABLE 3

Droplet Results for Two 45 kGy Electron Beam Irradiated Petri Dishes.

| Water Droplet Size (microLiters): | Dish 1, Droplets 1, 2, 3 (Degrees) | Dish 2, Droplets 1, 2 ,3 (Degrees) |
|---|---|---|
| 25 | 32, 32.5, 32 | 30, 31, 31 |
| 50 | 17, 18, 18 | 17.5, 17, 18 |
| 100 | 12, 12.5, 12.5 | 10.5, 11, 11.5 |

TABLE 4

Droplet Results for Two 55 kGy Electron Beam Irradiated Petri Dishes.

| Water Droplet Size (microLiters): | Dish 1, Droplets 1, 2, 3 (Degrees) | Dish 2, Droplets 1, 2, 3 (Degrees) |
|---|---|---|
| 25 | 28, 29 30 | 28, 27, 27 |
| 50 | 16, 17, 16.5 | 16.5, 16.5, 17 |
| 100 | 11, 12, 11 | 12, 11, 11.5 |

As water droplet mass was increased 4-fold (from 25 microLiters to 100 microLiters) the approximate elevation angle needed to initiate droplet movement decreased about 3-fold. Water droplet movement on Petri dish surface was initiated most easily (with the smallest angle of elevation) with the Petri dishes that were not irradiated. These non-irradiated dishes are therefore considered most hydrophobic. With electron beam irradiation, the most decrease in Petri dish hydrophobicity (e.g., increased water wettability and increased elevation angle to initiate water droplet movement on the Petri dish surface) was obtained with an electron dosage of 25 kGy with very little additional change above that electron dosage.

Example 3: Water Droplet Movement on 99% PLA with 1.0% PDA Petri Dishes

Petri dishes were molded by EcNow Tech Inc. by blending about 1% poly-D-lactide polymer with 99% poly-L-lactide polymer (weight/weight) as described in Examples 1 and 2, but these dishes were molded using different batches of polylactide resins. Before testing, each Petri dish was washed with distilled water. An X marking was placed on the outside of each dish near its center. The X marking was used to monitor initiation of movement of a water droplet placed above that marking after tilting each Petri dish at increasingly steep angles. Droplets of increasing micropipette-measured volumes (25, 50, and 100 microliters) of double-distilled water were applied to the bottom inside surface of each Petri dish, with the X marking on the outside of the Petri dish. Three droplets of each volume were tested on each Petri dish. Four non-irradiated Petri dishes were tested, two Petri dishes were tested for the 25 kGy irradiated condition, two Petri dishes were tested for the 40 kGy irradiated condition, and three Petri dishes were tested for the 55 kGy irradiated condition. The tilt angle for a Petri dish was set and measured using a protractor goniometer. Tables 6-8 summarize results for irradiated Petri dishes. Table 5 summarizes results for non-irradiated Petri dishes, and the measured elevation angle (using the protractor goniometer) is shown in degrees for each Petri dish and each droplet.

TABLE 5

Droplet Results for Four Non-Irradiated Petri Dishes.

| Water Droplet Size (microLiters): | Dish 1, Droplets 1, 2, 3 (Degrees) | Dish 2, Droplets 1, 2, 3 (Degrees) | Dish 3, Droplets 1, 2, 3 (Degrees) | Dish 4, Droplets 1, 2, 3 (Degrees) |
|---|---|---|---|---|
| 25 | 34, 35, 37 | 31, 30, 29 | 33, 34, 34 | 34, 33, 34 |
| 50 | 21, 22, 22 | 18, 19, 20 | 21, 20, 22 | 22, 23, 23 |
| 100 | 15, 16, 17.5 | 13.5, 14, 14 | 14, 13, 12 | 14, 15, 14 |

TABLE 6

Droplet Results for Two 25 kGy Electron Beam Irradiated Petri Dishes.

| Water Droplet Size (microLiters): | Dish 1, Droplets 1, 2, 3 (Degrees) | Dish 2, Droplets 1, 2, 3 (Degrees) |
|---|---|---|
| 25 | 44, 45, 44 | 44, 44, 45 |
| 50 | 25, 26, 26 | 24 25, 26 |
| 100 | 17, 16, 16 | 17, 17, 16 |

TABLE 7

Droplet Results for Two 40 kGy Electron Beam Irradiated Petri Dishes.

| Water Droplet Size (microLiters): | Dish 1, Droplets 1, 2, 3 (Degrees) | Dish 2, Droplets 1, 2, 3 (Degrees) |
|---|---|---|
| 25 | 44, 43, 45 | 38, 37, 37 |
| 50 | 28, 29, 28 | 23, 24, 25 |
| 100 | 17, 18, 17 | 15, 14, 14 |

TABLE 8

Droplet Results for Three 55 kGy Electron Beam Irradiated Petri Dishes.

| Water Droplet Size (microLiters): | Dish 1, Droplets 1, 2, 3 (Degrees) | Dish 2, Droplets 1, 2, 3 (Degrees) | Dish 3, Droplets 1, 2, 3 (Degrees) |
|---|---|---|---|
| 25 | 39, 37, 38 | 40, 37, 38 | 37, 39, 40 |
| 50 | 25, 26, 26 | 26, 25, 25 | 25, 24, 24 |
| 100 | 16, 15, 17 | 17, 16, 17 | 15, 14, 16 |

Only the non-irradiated Petri dishes showed droplet movement commencing with a lesser/shallower elevation being sufficient for each size of droplet. This observation indicates greater hydrophobicity for the non-irradiated Petri dishes. There was little incremental change with further irradiation beyond 25 kGy. With electron beam irradiation, the most decrease in Petri dish hydrophobicity (e.g., increased water wettability and increased elevation angle to initiate water droplet movement on the Petri dish surface) was obtained with an electron dosage of 25 kGy with very little additional change above that electron dosage.

Comparing elevation angle results for the various water droplet sizes on irradiated and non-irradiated dishes in Example 3 with those corresponding results in Example 2, it is apparent that the trending of results was similar in both Examples. However, the absolute elevation angles measured in Example 3 for the non-irradiated dishes were approximately twice as great as those in Example 2 (while the elevation angles for the irradiated dishes were approximately 50% greater). These results may indicate that the polylactide surfaces of the dishes in Example 3 were somewhat more hydrophilic than those in Example 2 (molded from different batches of resin).

Example 4: Cell Adhesion and Adherent Cell Culture

Experiments were conducted to investigate how mammalian cell growth on a mixture of poly-L-lactide and poly-D-lactide is affected under controlled cell culturing conditions. Three well-established mammalian cell lines were employed in testing cell growth, substrate adhesion, and viability, including HEK293 suspension-adapted cells, HEK293 adherent cells, and COS adherent cells.

Cells were cultured in DMEM medium (Dulbecco's Modified Eagles Medium) supplemented with 10% fetal bovine serum, 2 mM L-glutamine, and 100 I.U./ml each of penicillin and streptomycin in a 37° C. incubator with an atmosphere of 5% $CO_2$ in air. As negative and positive culturing "controls", the above three cell lines were cultured in either (i) sterile unmodified polystyrene Petri dishes suitable for bacteriological and yeast culture or (ii) sterile CellBIND® surface-treated polystyrene Petri dishes from Corning, Inc. suitable for mammalian cell culture. Within 3-5 days incubation in the first set of dishes (i), no cell adhesion was observed and microscopically all cells appeared dead. In the second set of dishes (ii) all cells appeared viable and the HEK293 and COS adherent cells were attached and growing in monolayers. These results confirm that modification of conventional thermoplastic surfaces such as polystyrene is needed for anchorage and growth of multiple varieties of mammalian cells Next, 90 mm diameter Petri dishes that were injection-molded by EcNow Tech, Inc. (Albany, Oreg.) using melt blends that combined approximately 1% poly-D-lactide and 99% poly-L-lactide were tested. These enantiomer polymer-blend Petri dishes (abbreviated "EP blend" dishes) were thermally annealed to promote the crystallization of the mixture of PLA/PDA and to provide thermal stability. Depending upon the annealing conditions of the PLA/PDA mixture, including but not limited to temperature and dwell time, thermal stabilities exceeding at least 60° C., or at least 65° C., or at least 70° C., or at least 75° C., or at least 80° C., or at least 85° C., or at least 90° C. were achieved. Thermal stabilities were evaluated by incubating the EP blend dishes in air for 30 minutes at the testing temperature and observing whether any visible warping of the flat bottom of the dishes had occurred. Following molding, the EP blend dishes were packaged in plastic film sleeves and sent out for sterilization using two different methods: One group was irradiated using cobalt 60 gamma irradiation (@25 kGy dosage) and two groups were irradiated using electron beam irradiation (@25 kGy dosage and @55 kGy dosage at 1 MeV electron energy).

The above 3 groups of sterilized EP blend dishes were biologically tested using the same three cell lines described above cultured in the same DMEM medium (see above). Remarkably, in the absence of any added surface treatment or modification of the EP blend PLA/PDA surfaces, when the above HEK293 adherent cells were seeded on the bottom interior surfaces of all three sterilized groups of the EP blend PLA/PDA dishes, the cells settled to approximately 25% confluence and grew steadily as monolayers to approximately 80% confluence within 72 hours. No differences in growth rates, cellular adhesion or cellular morphologies could be discerned among the dishes that had been sterilized using the three different protocols. Incubation with trypsin allowed easy detachment of the HEK293 adherent cells in all PLA/PDA dishes for subsequent passage. By comparison, the COS adherent cells that had been seeded in somewhat larger cellular patches, reached over 100% confluence in less than 72 hours. These somewhat overgrown cells were more tightly adhered to the substrate surface than the HEK293 adherent cells and were more difficult to detach even with trypsin incubation and vigorous agitation. Beneficially, however, with a lower seeding density these same cells grown for 72 hours without overgrowth were easily detached with trypsin incubation and successfully passaged. Finally, the suspension-adapted HEK293 cells grew at approximately the same rate over 72 hours as the HEK293 adherent cells, reaching approximately 60% confluence with more loosely adhered cells that were efficiently detached with trypsin, and with the balance of viable cells in suspended patches with no apparent loss in cellular viability.

For comparison purposes, the same three cell lines were simultaneously and successfully cultured on CellBIND® surface-treated polystyrene Petri dishes (Corning, Inc.) and grew with cellular morphologies and growth rates that were indistinguishable from the growth patterns on the EP blend PLA/PDA dishes. By contrast, failure of these same three cell types to adhere and/or grow on plain (unmodified/uncoated) polystyrene Petri dish surfaces that are suitable for bacteriological and yeast culture was previously described above.

Example 5: Bacterial and Yeast Cell Culture

Regarding the ability to carry out normal diagnostic bacterial cell culturing on gelled nutrient agar surfaces in the same EP blend PLA/PDA dishes as described in Example 1, the growth of *E. coli* cells was monitored in PLA/PDA dishes that had been cobalt 60-irradiated and sterilized (25 kGy dosage). Approximately 20 ml of Luria Broth (LB) bacterial growth medium (1% tryptone, 1% NaCl, and 0.5% yeast extract in water) with or without ampicillin (amp) antibiotic (100 micrograms per ml) and further containing 2% dissolved agar was poured into each dish at a temperature of 55° C. After agar solidification, both amp-sensitive and amp-resistant strains of *E. coli* were streaked out and incubated at 37° C. As a "positive control" a dish containing LB agar lacking any antibiotic allowed both amp-sensitive and amp-resistant cells to grow normally overnight. In dishes containing LB agar+antibiotic, the amp-resistant cells grew but not the amp-sensitive cells as anticipated.

Regarding the ability to carry out normal diagnostic yeast cell culturing on gelled nutrient agar surfaces in the same EP blend PLA/PDA dishes, the growth of *S. cerevisiae* yeast cells was monitored in these PLA/PDA dishes that had been cobalt 60 gamma-irradiated and sterilized (25 kGy dosage). Approximately 20 ml of YEPD medium (2% Bacto peptone, 1% yeast extract and 2% dextrose in water) and further containing 2% dissolved agar was poured into each PLA/PDA dish at a temperature of 55° C. After agar solidification, *S. cerevisiae* yeast cells were streaked out on the medium and incubated overnight at 30° C. The yeast cells grew normally and rapidly on the agar-gelled YEPD surface. Similarly, normal growth rates were observed for *S. cerevisiae* cells streaked out on minimal defined media contained in the same EP blend PLA/PDA dishes. Finally, microscopic examination of *S. cerevisiae* cells that had been plated out and incubated at 30° C. on a yeast sporulation medium supplemented with 1% potassium acetate and formulated to induce sporulation (also contained in identical EP blend PLA/PDA dishes) showed that the yeast cells experienced normal rates of sporulation with formation of normal four spore tetrads.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

What is claimed is:

1. A cell culture container consisting essentially of a polylactide polymer material, the material consisting of (100−X) wt % of poly-L-lactide and X wt % of poly-D-lactide, wherein X≤10, wherein 100 wt % represents the total weight of polylactide polymers in the material, and wherein the cell culture container is formed from the polymer material by a forced flow molding method and has been sterilized by gamma irradiation or electron beam irradiation, thereby increasing the hydrophilicity of a cell growth surface of the container compared to the cell growth surface without said irradiation.

2. The cell culture container of claim 1, wherein the forced flow molding method is selected from the group consisting of blow molding, rotational blow molding, injection blow molding, injection stretch blow molding, extrusion molding, extrusion molding followed by thermoforming, thin-wall injection molding, micro injection molding, and gas-assisted injection molding.

3. The cell culture container of claim 1, wherein the container is biodegradable.

4. The cell culture container of claim 1, wherein the container is compostable.

5. The cell culture container of claim 1, wherein the material is transparent.

6. The cell culture container of claim 1 that is viability-sustaining for a live culture of anchorage-dependent cells.

7. The cell culture container of claim 1 that is viability-sustaining for a live culture of suspension-growing cells, suspension-adapted cells, anchorage-dependent cells, and cells growing on a gelled culture medium.

8. The cell culture container of claim 1, wherein the container is configured as a container selected from the group consisting of a Petri dish, a cell culture flask, a multi-well plate, and a roller bottle.

9. The cell culture container of claim 1, including one or more cell growth structures selected from the group consisting of channels, lattices, matrices, webs, sponges, fibers, scaffolds, and beads; wherein said one or more cell growth structures consist essentially of a polylactide polymer material, the material consisting essentially of (100−X) wt % of poly-L-lactide and up to X wt % of poly-D-lactide, wherein X≤10, and wherein 100 wt % represents the total weight of polylactide polymers in the mixture.

10. The cell culture container of claim 1, wherein said cell growth surface of the container is devoid of any surface coating or chemical or physical surface modification other than by gamma irradiation or electron beam irradiation.

11. The cell culture container of claim 1, wherein X=0.

12. The cell culture container of claim 1, wherein said irradiation is at a dose in the range from about 25 kGy to about 55 kGy.

13. The cell culture container of claim 1, wherein the increase in hydrophilicity is associated with an increase in tilt angle of a water droplet on said cell growth surface after said gamma irradiation or electron beam irradiation.

14. A cell growth structure consisting essentially of a polylactide polymer material consisting of (100−X) wt % of poly-L-lactide and X wt % of poly-D-lactide, wherein X≤10, and wherein the cell growth structure is formed by a forced flow molding method and has been sterilized by gamma irradiation or electron beam irradiation, thereby increasing the hydrophilicity of a cell growth surface of the cell growth structure compared to the cell growth surface without said irradiation.

15. The cell growth structure of claim 14, wherein the forced flow molding method is selected from the group consisting of blow molding, rotational blow molding, injection blow molding, injection stretch blow molding, extrusion molding, extrusion followed by thermoforming, thin-wall injection molding, micro injection molding, and gas-assisted injection molding.

16. A method of making a cell culture container, the method comprising:
(a) heating a polylactide polymer material consisting of (100−X) wt % of poly-L-lactide and X wt % of poly-D-lactide, wherein X≤10 to a molding temperature, and wherein 100 wt % represents the total weight of polylactide polymers in the mixture;
(b) subjecting the material to a molding method comprising forced flow molding to form a structure having a shape of said cell culture container;
(c) cooling the structure;
(d) optionally annealing the structure for an annealing time at an annealing temperature; and
(e) sterilizing the container obtained from step (c) or step (d) with gamma irradiation or electron beam irradiation;
whereby said cell culture container is obtained.

17. The method of claim 16, wherein the forced flow molding method is selected from the group consisting of blow molding, rotational blow molding, injection blow molding, injection stretch blow molding, extrusion molding, extrusion followed by thermoforming, thin-wall injection molding, micro injection molding, and gas-assisted injection molding.

18. A method of culturing cells, the method comprising:
(a) providing the cell culture container of claim 1;
(b) adding cells and a culture medium to the container; and
(c) incubating the container, cells, and culture medium for an incubation time and at an incubation temperature such that the cells are viably sustained and optionally reproduce.

19. The method of claim 18, further comprising after step (c):
(d) allowing the container to be biodegraded and/or composted.

20. The method of claim 19, wherein the cells comprise an anchorage-dependent cell type, and wherein the anchorage-dependent cell type adheres to said growth surface of the cell culture container, wherein said growth surface is devoid of any surface coating or chemical or physical surface modification other than by gamma irradiation or electron beam irradiation.

* * * * *